(12) United States Patent
Jokinen et al.

(10) Patent No.: US 7,897,166 B1
(45) Date of Patent: Mar. 1, 2011

(54) BIODEGRADABLE CERAMIC FIBRES FROM SILICA SOLS

(75) Inventors: Mika Jokinen, Turku (FI); Timo Peltola, Turku (FI); Sinikka Veittola, Tampere (FI); Manja Ahola, Turku (FI); Pirjo Kortesuo, Turku (FI)

(73) Assignee: DelSiTech Oy, Turku (FI)

( * ) Notice: Subject to any disclaimer, the term of this patent is extended or adjusted under 35 U.S.C. 154(b) by 1128 days.

(21) Appl. No.: 09/913,643

(22) PCT Filed: Feb. 21, 2000

(86) PCT No.: PCT/FI00/00131
§ 371 (c)(1),
(2), (4) Date: Oct. 19, 2001

(87) PCT Pub. No.: WO00/50349
PCT Pub. Date: Aug. 31, 2000

Related U.S. Application Data

(60) Provisional application No. 60/121,180, filed on Feb. 22, 1999.

(51) Int. Cl.
*A61F 2/00* (2006.01)
*A61F 13/00* (2006.01)
*A61K 31/74* (2006.01)

(52) U.S. Cl. ............... 424/426; 424/422; 424/78.08
(58) Field of Classification Search ............... 424/426, 424/422, 78.08
See application file for complete search history.

(56) References Cited

U.S. PATENT DOCUMENTS

| | | | | |
|---|---|---|---|---|
| 4,895,709 | A | | 1/1990 | Laine ..................... 423/344 |
| 4,919,871 | A | * | 4/1990 | Lin et al. .................. 264/82 |
| 4,965,128 | A | | 10/1990 | Greidanus et al. ........ 428/398 |
| 5,342,595 | A | | 8/1994 | Davidovits et al. ...... 423/328.1 |
| 6,632,412 | B2 | * | 10/2003 | Peltola et al. .............. 423/338 |

FOREIGN PATENT DOCUMENTS

| | | | |
|---|---|---|---|
| DE | 196 09 551 | * | 12/1996 |
| DE | 196 09 551 | | 7/1997 |
| EP | 0 253 554 | | 1/1988 |
| EP | 0 336 014 | | 10/1989 |
| WO | WO 95/28124 | | 10/1995 |
| WO | WO 96/14274 | | 5/1996 |
| WO | WO 97/45367 | * | 12/1997 |

OTHER PUBLICATIONS

Kursawe et al., "Biodegradable Silica Fibres From Sols," 13 *J. Sol-Gel Sci. & Tech.* 267-271 (1998).

* cited by examiner

*Primary Examiner* — Blessing M Fubara
(74) *Attorney, Agent, or Firm* — James C. Lydon

(57) ABSTRACT

A method for preparing controllably biodegradable silica fibres which includes spinning the fibres from a silica sol of controlled viscosity, controllably biodegradable silica fibres prepared according to the method, methods for controlling the biodegradability of the fibres, the use of controllably biodegradable fibres as sustained and/or controlled release delivery devices for biologically active agents, and pharmaceutical preparations containing such devices.

10 Claims, 14 Drawing Sheets

BIODEGRADABLE CERAMIC FIBRES FROM SILICA SOLS

This application is a U.S. national stage of International Application PCT/FI00/00131, filed Feb. 21, 2000, which claims priority of U.S. provisional application No. 60/121,180, filed Feb. 22, 1999.

TECHNICAL FIELD OF THE INVENTION

The present invention is directed to methods for preparing controllably biodegradable silica fibres. Specifically, the present invention is directed to methods for preparing controllably biodegradable silica fibres comprising spinning the fibres from a silica sol, the viscosity of the sol being controlled. Further, the invention is directed to controllably biodegradable silica fibres prepared according to the present invention. The invention is further directed to methods for controlling the biodegradation of the silica fibres. The invention is also directed to controllably biodegradable fibres as sustained and/or controlled release delivery devices for biologically active agents, especially medicines, proteins, or hormones, and to pharmaceutical preparations comprising the devices.

BACKGROUND OF THE INVENTION

The sol-gel derived ceramic materials have many applications in various fields. Bioceramics is one of the most promising and interesting fields that still need much development work for optimizing the properties of the material in the biological environment. The sol-gel process starting from a liquid phase enables an easy control of the pore structure of the material and an introduction of other components in different kinds of composites, especially, in the case of silica-based materials. The processing of the sol-gel derived silica fibres is known, and the main parameters controlling the process are the functionality of the silica precursors, or the degree of branching of the silica clusters. The latter critically affects the spinnability and has commonly been characterised by rheological measurements.

Fibres have traditionally been used to improve mechanical properties of materials. In the case of the sol-gel derived silica fibres, there are two main parameters that determine the fibre bulk structure. Heat treatment of the fibres is one way to condense the bulk structure. Depending on the application of the sol-gel derived biodegradable silica fibres, the balance between mechanical properties and biodegradation may vary. For example, the mechanical properties are of minor importance when the silica fibre is used as a drug delivery device in a soft tissue. However, the mechanical properties have to be good enough to further process the obtained fibres to a desired form after spinning. The biodegradation of the silica fibre decreases remarkably after heat-treatment at high temperatures simultaneously as the mechanical properties become better.

International patent publication No. WO 97/45367 discusses sol-gel produced silica-xerogel materials. Patent publication DE 19609551 discusses silica fibers obtained by drawing them from a specific spinning composition. Neither of the patent publications teaches or suggests a controllably biodgradable silica fibre, a delivery device, or a pharmaceutical composition according to the invention or methods for preparing or using the same. Further, neither of the patent publications teaches or suggests a method according to the invention for controlling the biodegradation of a silica fibre.

SUMMARY OF THE INVENTION

It has been found that the biodegradation of silica fibres can be controlled by controlling the viscosity of the spinning solution and, thus, the biodegradation of the silica fibres can be varied even when the same recipe is used. Accordingly, an object of the present invention is to provide a method for preparing controllably biodegradable silica fibres. Specifically, the present invention provides a method for preparing a controllably biodegradable silica fibre, wherein the method comprises spinning the fibre from a silica sol, wherein the viscosity of the silica sol is controlled. More specifically, the present invention provides a method for preparing a controllably biodegradable silica fibre, wherein the method comprises spinning the fibre from a silica sol, wherein the starting point of the spinning process is controlled by the viscosity of the silica sol.

It should be noted that the term spinning encompasses all of the suitable methods for preparing silica fibres from a silica sol.

A further object of the invention is to provide a controllably biodegradable silica fibre spun from a silica sol. Specifically, the present invention provides a controllably biodegradable silica fibre spun from a silica sol, wherein the biodegradation of the fibre is controlled by controlling the viscosity of the spinning sol. More specifically, the present invention provides a controllably biodegradable silica fibre spun from a silica sol having a viscosity below 100 000 mPas (milliPascalsecond), preferably having a viscosity of 1000-50 000 mPas, and more preferably of 2000-15 000 mPas. The fibre of the present invention is preferably heat-treated, to initially dry the fibre, only at low temperatures not harmful to biologically active agents, and it is not otherwise externally densified.

A further object of the invention is to provide sustained and/or controlled release delivery devices for biologically active agents, especially medicines, proteins, or hormones which are made of controllably biodegradable silica fibres, and pharmaceutical preparations comprising said devices.

A further object of the present invention is a method for controlling the biodegradation of silica fibres. The method comprises controlling the viscosity of the spinning sol or controlling the viscosity of the silica sol at the starting point of the spinning process.

Also, an object of the present invention is to provide a method for administering a biologically active agent to a human or animal which comprises implanting, injecting, or mucosally attaching to a human or animal a delivery device made of controllably biodegradable silica fibres of the present invention, in which structure a biologically active agent is incorporated.

Figure 6:
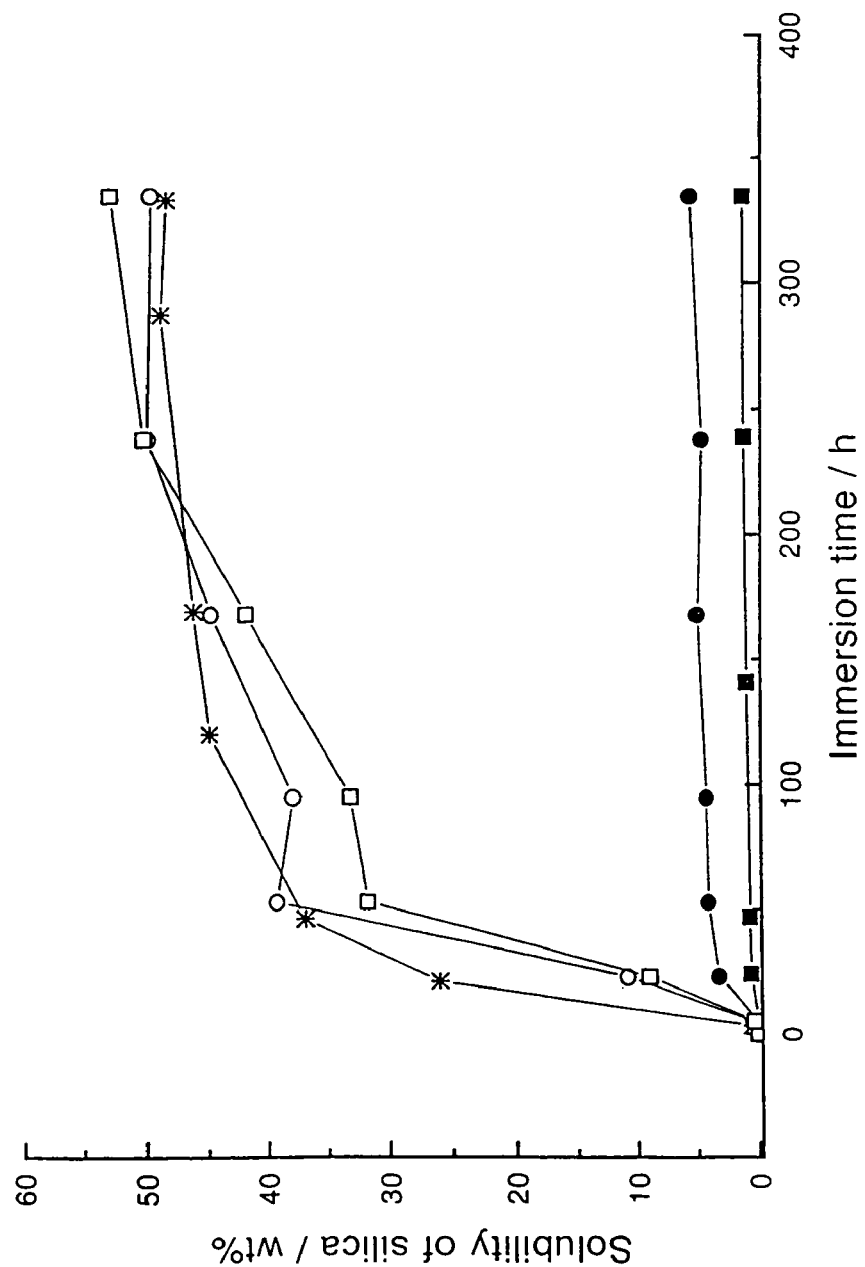

FIG. 6 shows the biodegradation of the green state fibres aged for 3 months. Closed square (■) FIB1_A, open square (□) FIB 1_B, closed circle (●) FIB2_A, open circle (○) FIB2_B, asterisk (✳)FIB3.

Figure 7:
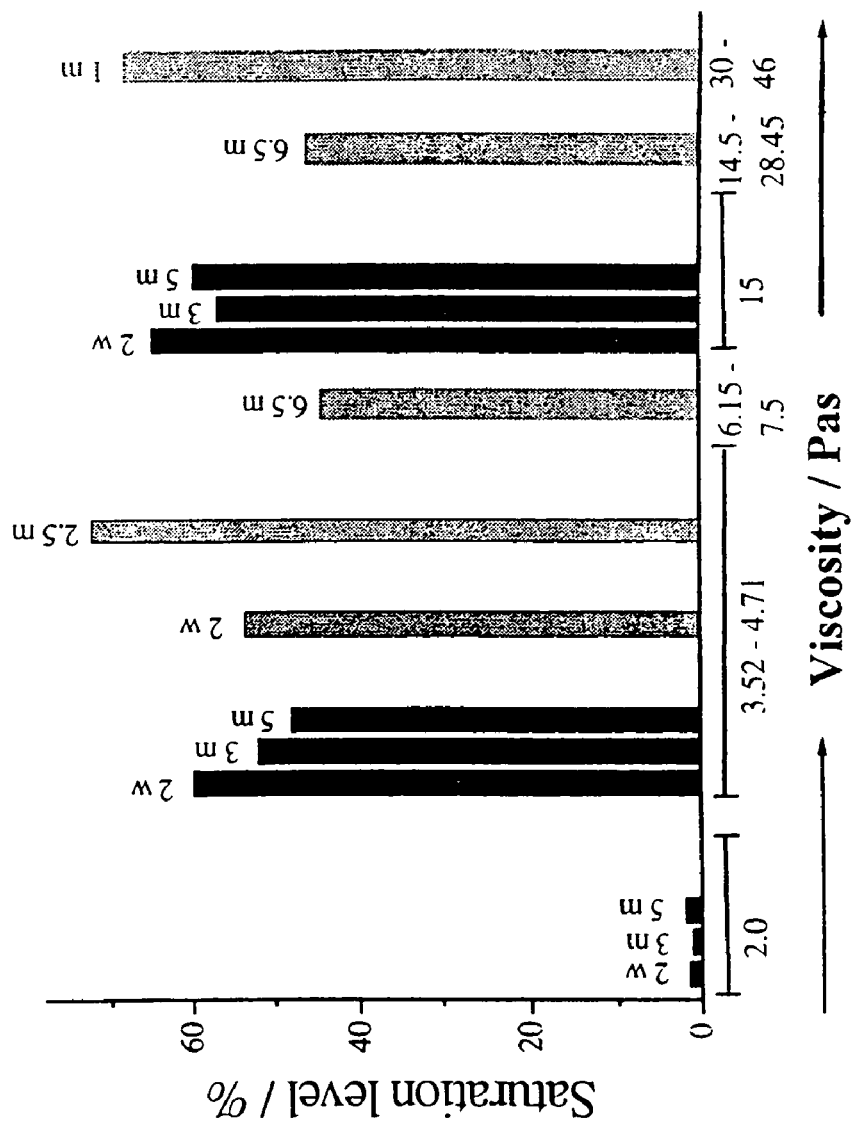

FIG. 7 shows the $SiO_2$ solubility measured as saturation level of silica in SBF as a function of sol viscosity at the starting point of the spinning process for FIB1 aged for various time periods.

Figure 8:
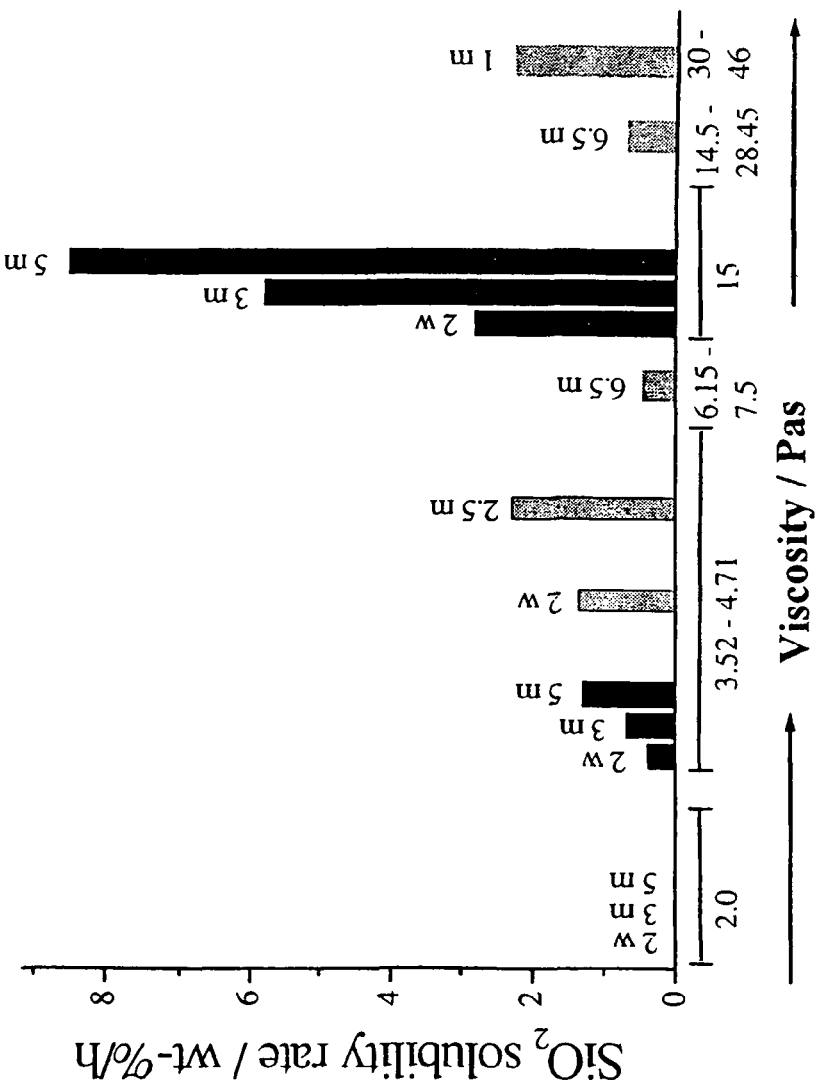

FIG. 8 shows the $SiO_2$ solubility in weight-% per hour in SBF as a function of sol viscosity at the starting point of the spinning process for FIB1 aged for various time periods.

Figure 9:
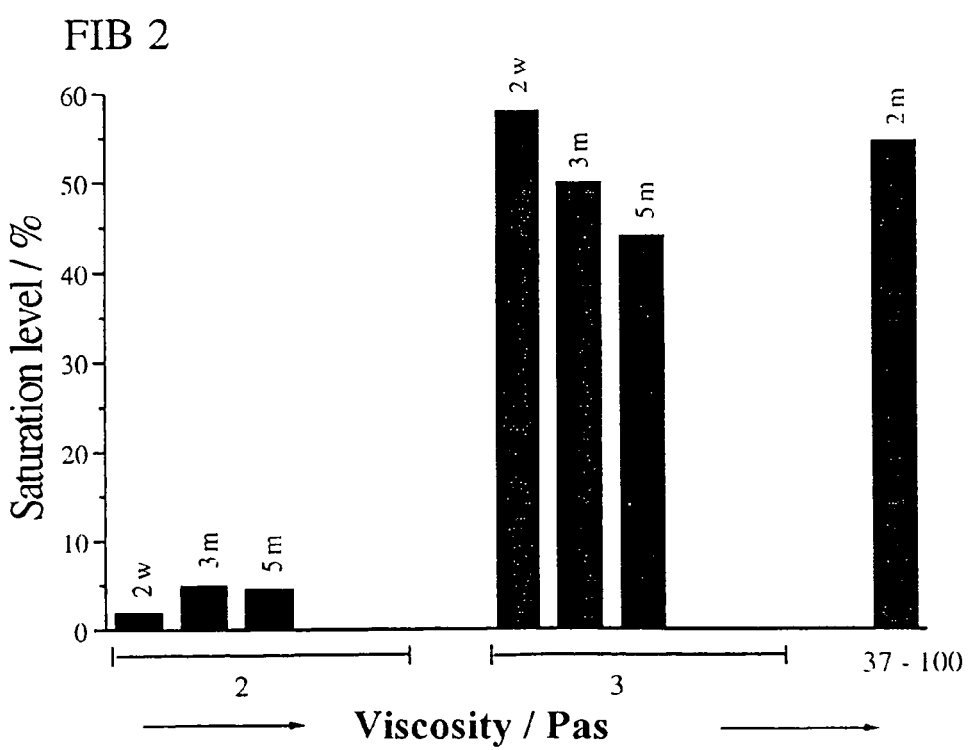

FIG. 9 shows the $SiO_2$ solubility measured as saturation level of silica in SBF as a function of sol viscosity at the starting point of the spinning process for FIB2 aged for various time periods.

Figure 10:
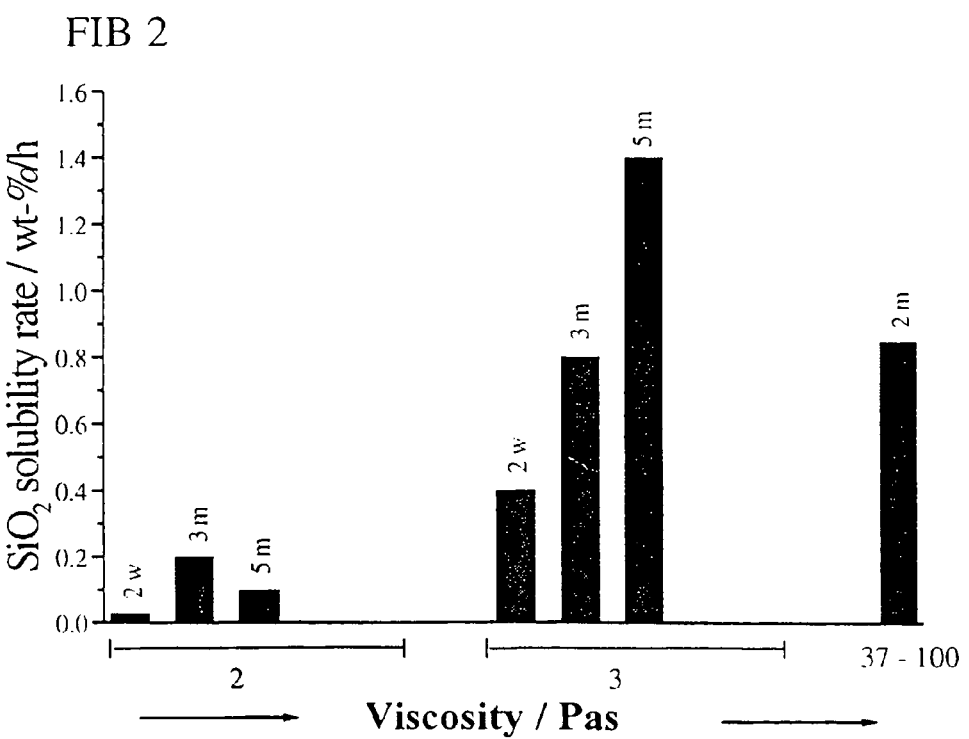

FIG. 10 shows the $SiO_2$ solubility in weight-% per hour in SBF as a function of sol viscosity at the starting point of the spinning process for FIB2 aged for various time periods.

Figure 11:
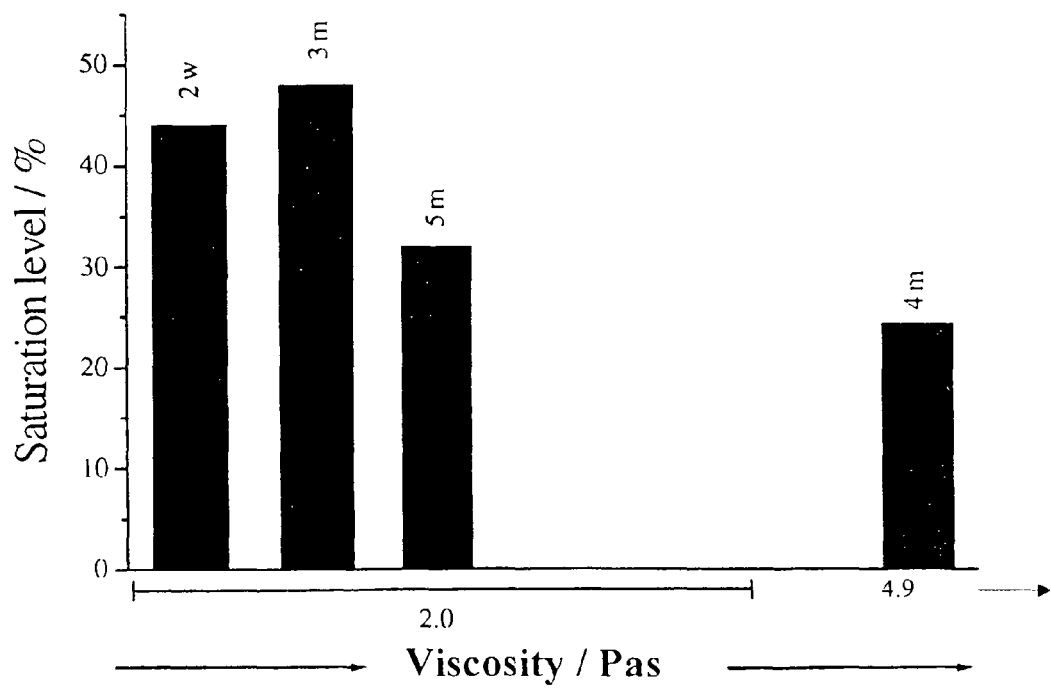

FIG. 11 shows the $SiO_2$ solubility measured as saturation level of silica in SBF as a function of sol viscosity at the starting point of the spinning process for FIB3 aged for various time periods.

Figure 12:
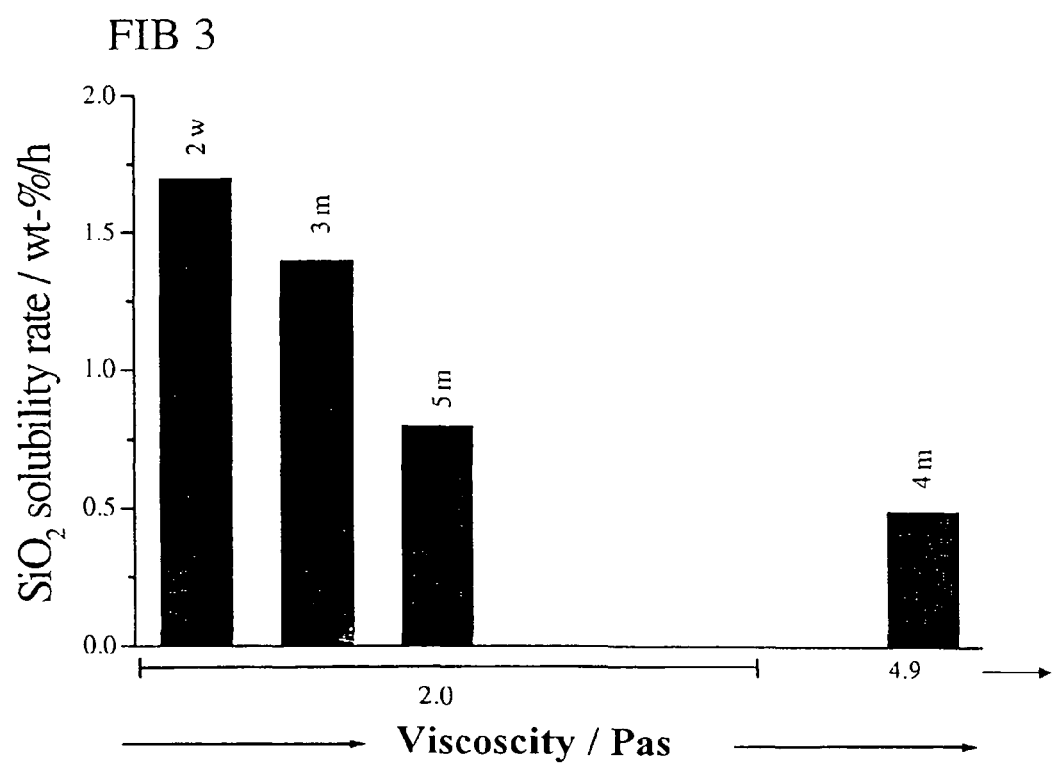

FIG. 12 shows the $SiO_2$ solubility in weight-% per hour in SBF as a function of sol viscosity at the starting point of the spinning process for FIB3 aged for various time periods.

Figure 13:
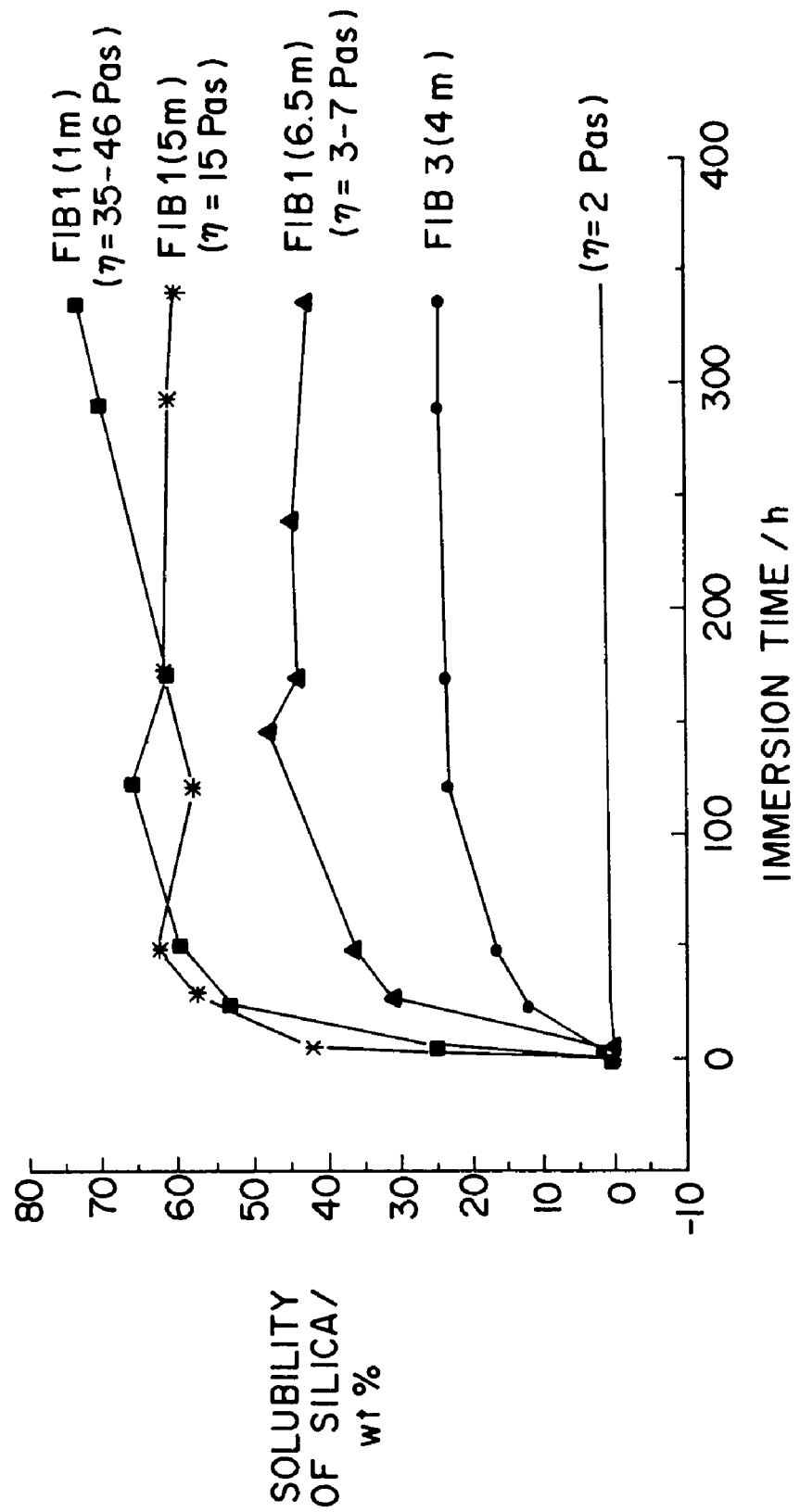

FIG. 13 shows the changes of $SiO_2$ concentration (wt-%) as a function of immersion time in the simulated body fluid for different fibres.

Figure 14:
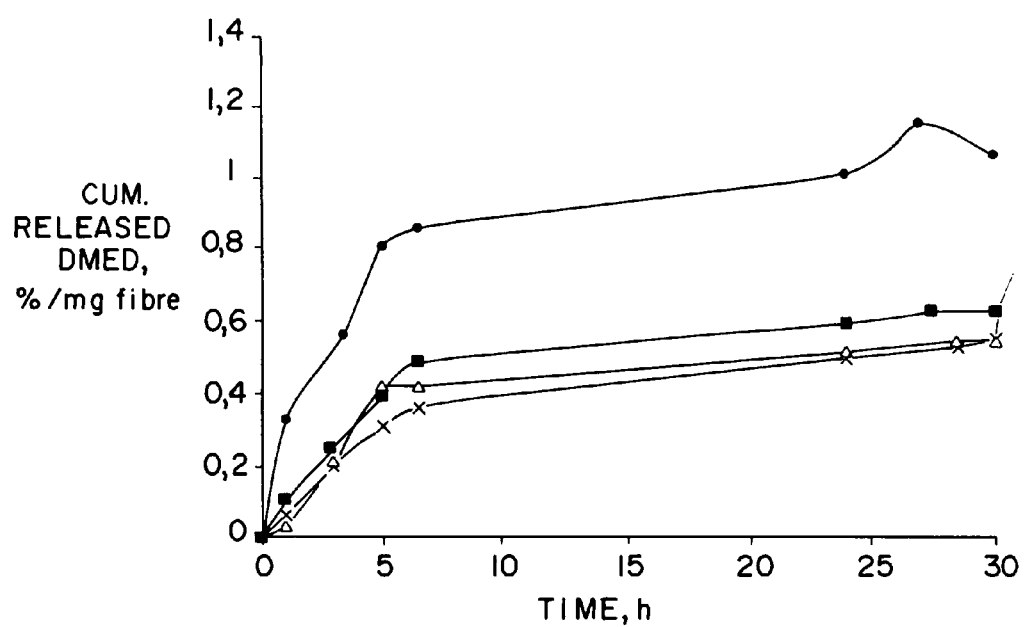

FIG. 14 shows the release of dexmedetomidine from the silica fibres of Example 4. Closed circle (●) 5600-7500 mPas, asterisk (✳) 11 500-14900 mPas, open triangle (Δ) 17 000-29 000 mPas, closed square (■) 39 000-100 000 Pas.

DESCRIPTION OF THE INVENTION

Applicants have discovered that the biodegradation of silica fibres can be controlled by controlling the viscosity of the spinning solution. The biodegradation of the fibres can be varied even when using the same recipe. The biodegradation of the fibres can be adjusted for desired purposes by controlling the viscosity of the spinning solution for determining the starting point of the spinning.

Factors affecting the viscosity are the stage of spinnability, the temperature of the silica sol and the amount of solvent in the spinning sol. The silica sol is spinnable within a certain time period, rather than at a single point, and the viscosity of the silica sol increases during that time period. In the earlier stage of spinnability the silica polymers are somewhat smaller and they are packed easier forming denser structures than the larger silica polymers of the later stage of spinnability. In addition, higher viscosity inhibits the orientation of the silica polymers leaving the structure more open. The fibres spun in the early stage of the spinnability period degrade more slowly in the simulated body fluid than the fibres spun in the later stage of the spinnability. The stage of spinnabilty may differ depending on the spinning method. Another parameter that controls the spinnability and the viscosity is the temperature of the silica sol which can be varied. The fibres spun from the silica sols having higher viscosity at a lower temperature (e.g., 0° C.) degrade faster than the corresponding fibres spun at higher temperatures (e.g., 20° C.).

The method for preparing a controllably biodegradable fibre of the present invention comprises spinning the fibre from a silica sol, wherein the starting point of the spinning process is controlled by the viscosity of the silica sol. The viscosity of the silica sol at the starting point of the spinning process is below 100 000 mPas. Preferably it varies in the range of 1000-50 000 mPas, and more preferably in the range of 2000-15 000 mPas.

Another method according to the present invention comprises spinning or drawing the fibre from a spinning sol, wherein the viscosity of the silica sol is below 100 000 mPas, preferably in the range of 1000-50 000 mPas, and more preferably in the range of 2000-15 000 mPas.

The controllably biodegradable silica fibre of the present invention is spun from a silica sol, the biodegradation of the fibre being controlled by controlling the viscosity of the spinning sol or by controlling the starting point of the spinning process by the viscosity of the silica sol. Specifically, the fibres are spun from a silica sol having the viscosity of 1000-50 000 mPas, preferably 2000-15 000, the fibres having the solubility of 0.01-20 m-%/h, preferably 0.02-8.5 m-%/h in the simulated body fluid, respectively.

The silica sol can be prepared for example as described in WO 97/45367. For example, a silica sol can be prepared by allowing a silica-alkoxide, such as tetraethylorthosilicate (TEOS) or an organically modified silicate (ORMOSIL), to react with water and optionally an organic solvent, e.g. ethanol or polyethylene glycol, or a combination of solvents, at low temperature, such as −20° C. to 100° C., preferably near room temperature, in the presence of an acidic or a basic catalyst by hydrolysis and subsequent condensation reactions. The condensation may also be partial. The sol can be incorporated with ions, such as Na, K, Ca, P, Mg, Al and B. The catalyst should be such that it would not harm the biologically active agent.

The methods that can be used for preparing the silica fibres according to the present invention are known to those skilled in the art. A suitable method is any method suitable for preparing fibres from silica sol, and the term spinning is used in this context to describe any such method. The spinning techniques include, e.g., dry spinning or a centrifugal method. In the dry spinning method, the silica sol is forced through a spinneret and the evaporation of the solvent promotes the gelation. For example, the spinning solution is kept in a closed container and an inert gas, preferably nitrogen gas, is led to the container to push the spinning solution to a gear pump, wherein the spinning solution is metered to the spinneret. Preferably, the container is temperature adjustable. There are also special methods that are based on dry spinning. These methods include, e.g., a method wherein the fibre is led to a suitable aerosol which promotes the gelation of the fibre or a method wherein dry spinning and wet spinning are combined. In the centrifugal method, the spinning solution is in a rotating chamber which extrudes fibers through the holes in the chamber wall.

The controllably biodegradable fibres of the present invention can be used for delivery devices or pharmaceutical preparations that are, for example, implanted or injected into, or mucosally attached to a human or animal. Administration into any tissue, soft tissues or bone, is possible. This allows local application so that targeting of the biologically active agent release site is possible. Therefore, the maximum effect from the agent is received.

In this connection, a delivery device includes a silica fibre or a combination of silica fibres with a biologically active agent incorporated into the silica fibre structure. A pharmaceutical preparation, such as a granulate or capsule, in this context is a preparation that comprises the delivery device and possibly additional excipients useful in pharmaceutical preparations. A medical device of the invention is also useful for orthopedic and surgical purposes and need not contain a biologically active agent incorporated into its structure. A medical device may be, e.g., a woven or nonwoven mat made of silica fibres, a knitted fabric or a braided cord. The delivery devices and medical devices of the invention can be prepared by spinlaying.

The controllably biodegradable silica fibres of the invention may be either stable fibres or filaments. The silica fibres can be a part of a fibre blend or a part of some other material that is not in the fibre form.

Introduction of biologically active agents into the porous structure of the fibre provides alternatives for the design of biomedical applications. Biodegradable and non-toxic materials that are able to work directly and locally in the human or animal are beneficial, for example as implants used as drug delivery device or temporary implants in bone repairs. The sol-gel derived silica fibres according to the invention fulfill these requirements. The biologically active agents incorporated into the fibre structure are released controllably and they can be used for delivery devices or pharmaceutical preparations that are, for example, implanted or injected into, or mucosally attached to a human or animal. The biologically active agent can be any organic or inorganic agent that is biologically active. The biologically active agent can be, e.g., a medicine, a protein, a hormone, a living or dead cell, a bacteria, a virus or a part thereof. Biologically active agents include those especially useful for long-term therapy, such as hormonal treatment, e.g., contraception and hormone replacement therapy and for the treatment of osteoporosis, cancer, epilepsy, Parkinson's disease, pain, and cognitive dysfunction. The suitable biologically active agents may be, e.g., anti-inflammatory agents, anti-infectives (e.g., antibiotics and antiviral agents, such as glindamycin, miconazole), analgesics and analgesic combinations, antiasthmatic agents, anticonvulsants (e.g., oxycarbazepine), antidepressants, antidiabetic agents, antineoplastics, anticancer agents (e.g., toremifene, tamoxifene, taxol), antipsychotics, antispasmodics, anticholinergics, sympatomimetics, cardiovascular preparations, antiarrythmics, antihypertensives, diuretics, vasodilators, CNS (central nervous system) drugs such as antiparkinsonism dugs (e.g., selegiline), steroidal hormones (e.g., estradiol, progesterone, nestorone), sedatives (e.g., medetomidine, dexmedetomidine, levomedetomidine), tranquilizers, and cognitive dysfunction drugs (e.g., atipamezole). The medicine can be in the form of a salt, such as selegiline hydrochloride, (−)-4-(5-fluoro-2,3-dihydro-1H-inden-2-yl)-1H-imidazole hydrochloride, 4-(5-fluoro-2,3-dihydro-1H-inden-2-yl)-1H-imidazole hydrochloride, dexmedetomidine hydrochloride and toremifene citrate. The medicine can also be in the form of a free acid, such as ibuprofen; a free base, such as caffeine or miconatzole; or a neutral compound, such as Z-2-(4-(4-chloro-1,2-diphenyl-but-1-enyl)phenoxy) ethanol. A peptide can be e.g. levodopa, and a protein can be e.g., an enamel matrix derivative or a bone morphogenetic protein. An effective amount of a biologically active agent can be added to the reaction mixture at any stage of the process. For example, it can be mixed with the starting materials. It can also be added to the reaction mixture at the sol-stage before condensation reactions take place or during the condensation reactions, or even afterwards. The precise amount employed in a particular situation is dependent upon numerous factors, such as the method of administration, type of mammal, the condition for which the biologically active agent is administered, the particular biologically active agent used, the desired duration of use, etc.

The following examples are merely intended to ilustrate the present invention and not in any way to limit its scope.

EXAMPLES

Example 1

Preparation of Silica Sols for Spinning

The silica sols were prepared from TEOS (tetraethyl orthosilicate 98%, ALDRICH), deionised water (conductivity ~0.05 S), ethanol (Aa, 99.5%, ALKO) and $HNO_3$ (65%, Merck) or $NH_3$ (28%, Fluka) as catalysts using the sol-gel method. The molar ratios used are shown in Table 1.

TABLE 1

Sol compositions in molar ratios

| Name | Molar ratio (r) | | | |
|---|---|---|---|---|
| | $H_2O$/TEOS | EtOH/TEOS | HNO/TEOS | $NH_3$/TEOS |
| FIB1 (A&B) | 2 | 1 | 0.036 | 0 |
| FIB2 (A&B) | 2 | 1 | 0.1 | 0 |
| FIB3 | 2 | 1 | 0.1 | 0.01 |

The spinning solution was prepared as follows. Ethanol was mixed with TEOS and nitric acid with water. The acid/water solution was added to the TEOS/ethanol solution under vigorous stirring and then the solution was poured in an evaporating dish. The lid of the dish is a special cooler which condenses the evaporating ethanol and leads it to a volumetric flask. The evaporating dish was placed into a water bath (40° C.) and the solution was kept there until a desired amount of ethanol had evaporated (20-22 h). Evaporation of ethanol was used to reduce the overall process time after which all the sols were still spinnable. Table 2 shows theoretical silica concentrations of the spinning solutions assuming that the net reaction is $nSi(OR)_4 + 2nH_2O \rightarrow nSiO_2 + 4nROH$ and that the evaporating fraction consists mostly of ethanol due to relatively low temperature and low water content (r=1) that is mostly consumed in the hydrolysis.

TABLE 2

Silica content of the spinning solution

| Sample name | $m(SiO_2)/[m(SiO_2) + m(EtOH)]$/wt-% |
|---|---|
| FIB1_A | 45.4 |
| FIB1_B | 45.4 |
| FIB2_A | 42.7 |
| FIB2_B | 42.7 |
| FIB3 | 41.7 |

The sols were cooled to either 20° C. or 0° C. depending on the sample. When the spinning solution reached a certain level of viscosity the spinning was started. A rotational viscometer with a disc shaped spindle (Brookfield LVDV II+) was used to define the point where the spinning was started. Because of practical problems due to a great batch size of the spinning sols, the obtained viscosity values were not absolute, but they were comparable to each other. The initial viscosity was the same for all sample sols when the spinning process was started. However, each sol recipe was used to spin fibres in several stages. Air bubbles were removed from the spinning solution under partial vacuum. If this had not been done the sol-gel filaments would have broken due to a discontinuous flow of the spinning solution.

Dry spinning was used to prepare the sol-gel fibres. The spinning solution was kept in a container whose temperature is adjustable. Nitrogen gas was led into the closed container to push the spinning solution to a gear pump. Nitrogen is a good choice for this purpose because then the spinning solution is prevented to contact the humid air. The gear pump (Zenith 958736) with a capacity of 0.6 ml/revolution metered the spinning solution to the spinning head. The spinneret is made of a gold/platinum mixture. The diameter of the holes was 0.065 mm and the length/diameter (l/d) ratio was 1. The number of the holes was 6. The distance between the spinneret and the wind-up roll was adjusted to meet the demands of each fibre.

Example 2

Characterisation of the Fibre Structures

Figure 1:
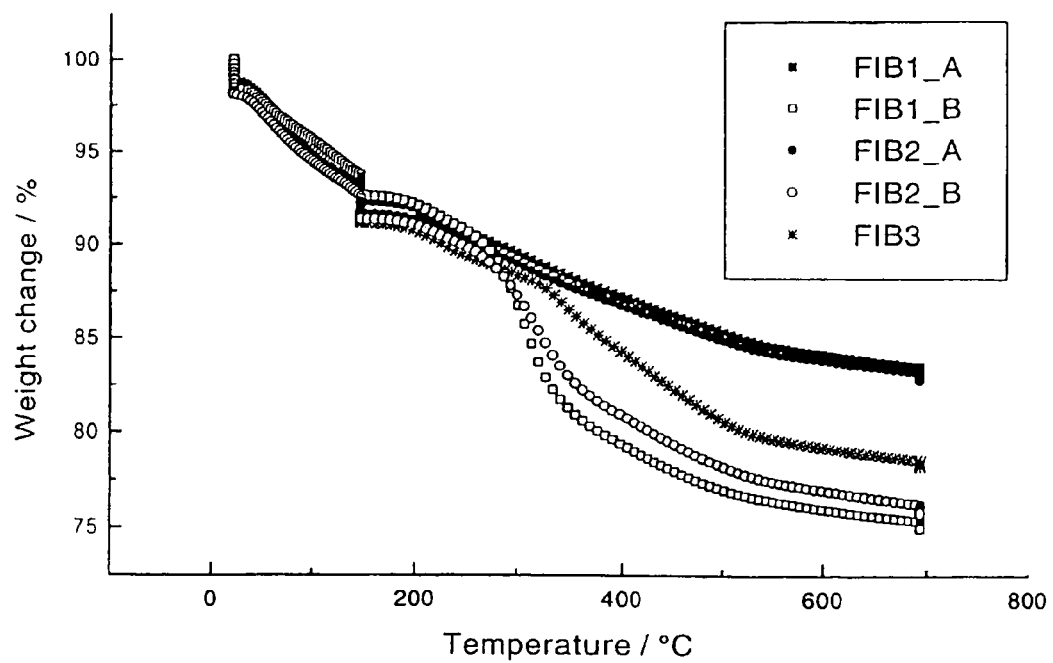
FIG. 1 shows a thermogravimetric spectra of the green state fibre samples aged for 3 months.
Figure 2:
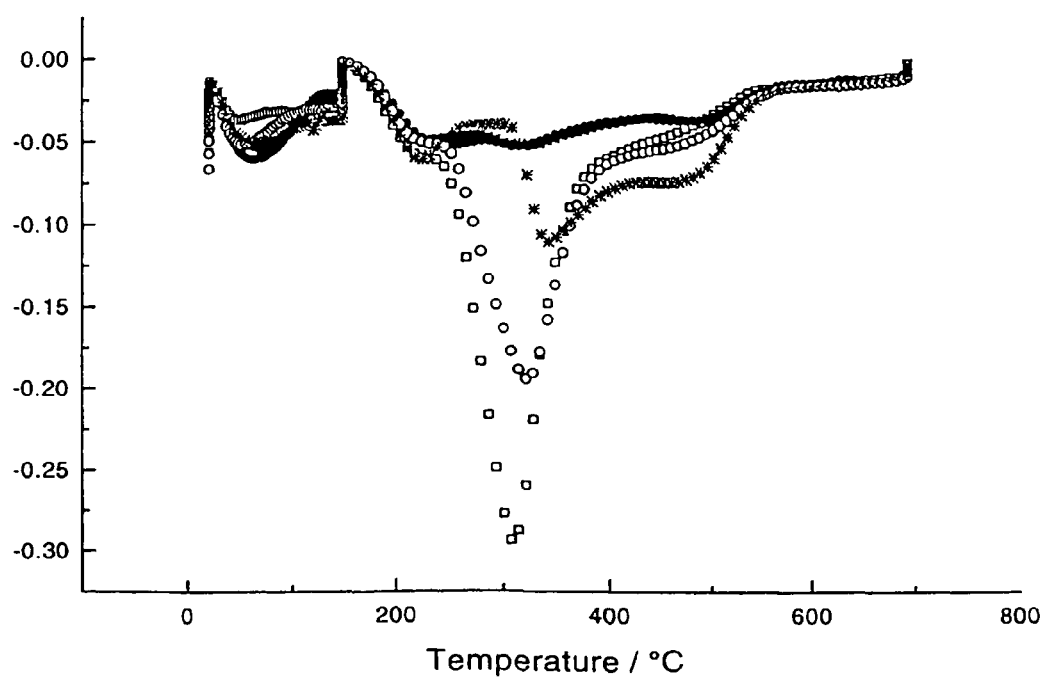
FIG. 2 shows a derivative of the thermogravimetric spectra of FIG. 1.

A thermogravimetric analysis (TGA) was performed on the green state fibres to measure weight changes with a Netzsch TG-209 equipment (NETZSCH GmbH, Selb, Bavaria, Germany) with nitrogen as the protective gas and air as the purge gas. The sample holder was a ceramic alumina crucible and the background measurement was done with an empty crucible before the measurements. The mass loss during the heat-treatment of the fibres was measured with a temperature program including several steps, both isothermal and dynamic: isothermal for 15 min at 21° C., dynamic 21-150° C. with 2° C./min, isothermal for 60 min at 150° C., dynamic 150-700° C. with 5° C./min and isothermal at 700° C. for 30 min. TGA was performed for the fibres aged in a desiccator at room temperature for 3 months. The analysis was done up to 700° C. because higher temperatures are practically useless concerning biodegradable applications of silica. The results of the samples are shown in FIG. 1, and the derivative of the spectra is shown in FIG. 2.

The physical appearance of the fibres and the quality of the fibre filament in the spinning process, shown in Table 2, seem to have a connection with the TGA measurements. The mass losses of the fibres were quite considerable (15-25%), which stresses that a careful control of the heat treatment is required in order to avoid cracking problems. The mass losses of the fibres spun in the early stage of spinnability was not as great as those spun in the later stage of spinnability. The greatest difference started at about 300° C., where the organic matter usually starts to evaporate. Because the recipes were exactly the same for FIB1_A and FIB 1_B, as well as for FIB2_A and FIB2_B, respectively, it is likely that some organic matter was captured in the fibre structure in the fibres spun in the early stage. Also the shift observed in the derivatives of the fibres spun in the later stage of spinnability (FIB1_B, FIB2_B and FIB3) indicates some differences in the evaporation of the organic matter and in the fibre structure. The physical appearance of the fibres contributes suggestions. The black colour of the fibres spun in the early stage of spinnability indicate that they contain carbon residuals. FIB3, where both $HNO_3$ and $NH_3$ were used as catalysts, had intermediate properties, both in the TG analysis and physical appearance. The mass loss is greater than in FIB1_A and FIB2_A, but smaller than in FIB1_B and FIB2_B. Also the colour of the FIB3 fibre was something between white and black, i.e., brown, and the filament quality in the spinning process had analogous properties. The best and continuous fibres were easiest achieved with FIB1_B and FIB2_B. There were some difficulties with FIB3, FIB1_A and FIB2_A (processed at 0° C. to achieve high enough viscosity in spinning). The filament broke easily and continuous fibre processing was more difficult.

Figure 3:
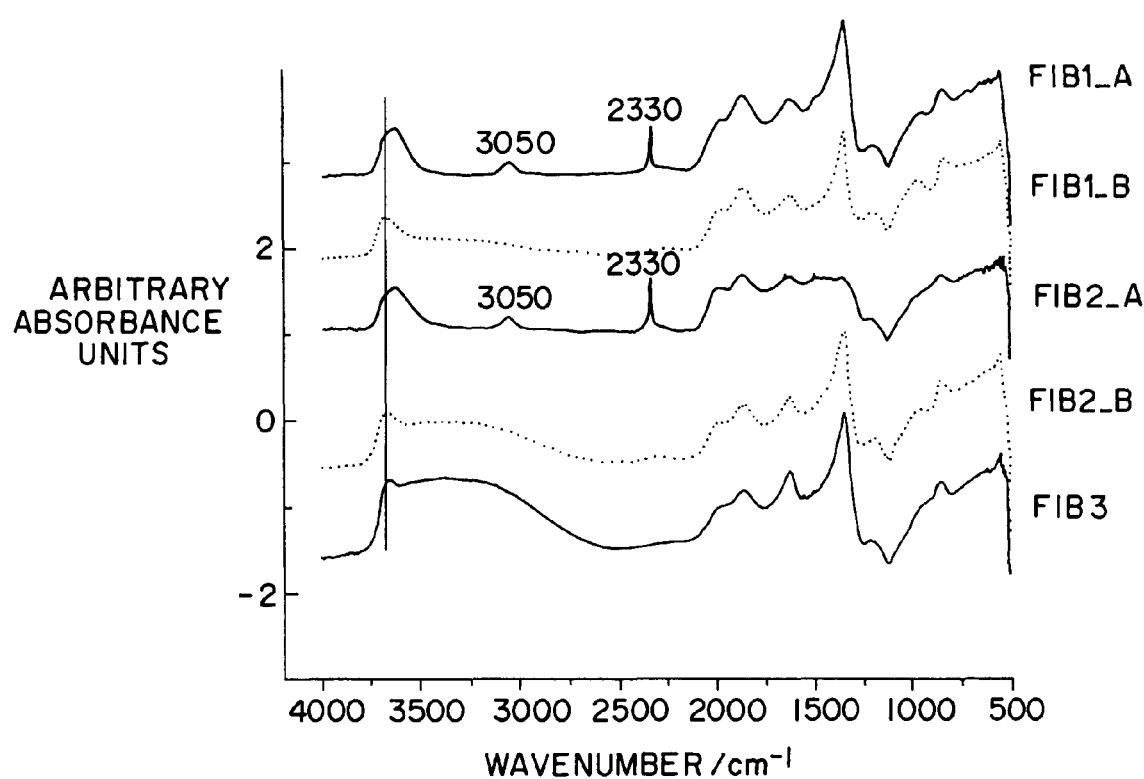
FIG. 3 shows an FT-IR spectra of the fibre samples heat-treated in the thermogravimetric analysis.

The infrared absorption spectra were recorded between 400 and 4000 $cm^{-1}$ using Bruker IFS 66 FTIR spectrometry. The measurements were carried out with the Diffuse Reflectance Infrared Fourier Transformation (DRIFT) system. Potassium bromide was used as a background material. The resolution of the FTIR equipment was 4 $cm^{-1}$. The FT-IR measurements made for the fibres heat-treated in the thermogravimetric analysis are shown in FIG. 3. The measurements gave information of the typical OH groups on the silica surface, but also two unusual peaks were detected in the fibres spun in the early stage of spinnability (FIB1_A and FIB2_A). The broad peak at 3400-3770 $cm^{-1}$ includes peaks related to isolated single SiOH groups, isolated geminal groups, H-bonded hydroxyls and physically adsorbed water which additionally has a peak approximately at 1630 $cm^{-1}$ (broad). Additionally, the shift in the peaks indicated by a line drawn in the graph suggested that some organic residuals were also detected here. The shift was analogous with the extra peaks observed for FIB1_A and FIB2_A and the slight shift for FIB3 contributed the intermediate physical appearance. Peaks related to Si—O—Si vibrations were observed at 1200-1100 (broad) and 800 $cm^{-1}$. The peaks at 1870 and 2000 $cm^{-1}$ were the Si—O—Si overtone bands of silica. The peak at 1300-1400 $cm^{-1}$ was not typical for silica, but $NO_3^-$ stretching vibration was typically located there. The catalyst used in the sol preparation process was $HNO_3$, which may have residuals left in the structure. The fibre structure was commonly condensed and the temperature increased from 450 to 700° C. quite fast and was kept there only for 30 min. This means that the decomposition of nitrate was not very effective. The two interesting peaks at 2330 and 3050 $cm^{-1}$ were clearly seen only for FIB 1_A and FIB2_A, but they could not be directly related to any component present in the system. The only possibility was that the fibres contained carbon residuals which formed double bonds with hydrogen (3050 $cm^{-1}$) and oxygen (2330 $cm^-$) observed at these points.

Figure 4:
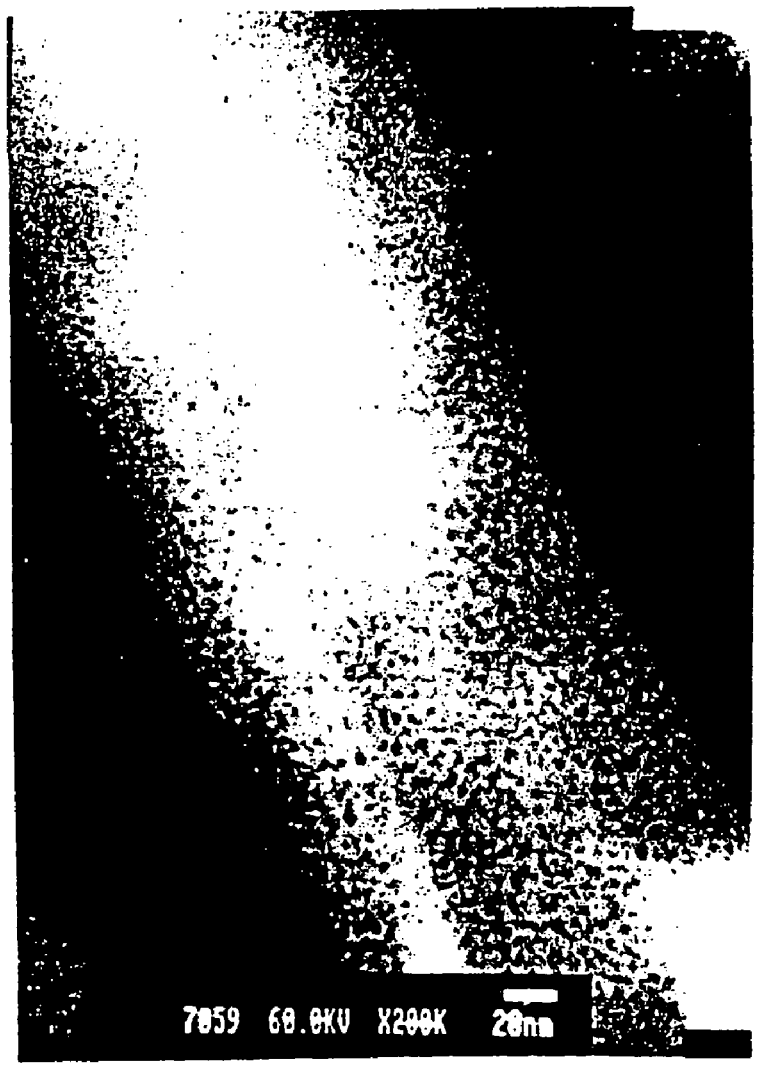
FIG. 4 shows a transmission electron micrograph of the green body of FIB2_B aged for 3 months.

A scanning-transmission electron microscopy (JEOL, JEM 1200 EX) was used to illustrate the bulk structure of the green state fibres. The fibres were embedded in an epoxy resin (EPON 812). Propylene oxide was used as a solvent and epoxy embedding media DMP-30 and DDSA or MNA as an accelerator and hardeners (FLUKA), respectively. The hardened samples were cut with an ultramicrotome to a thickness of 60-70 nm and the cross sections of the fibres were analysed. A transmission electron micrograph of the cross section of FIB2_B is shown in FIG. 4. The image was chosen as an example to show the inner structure of the sol-gel derived silica fibres. The images of all five samples reminded each other. FIB2_B was suggested to be a representative example of the fibres because the filament quality was good and the fibres were easy to prepare. The white bar at the bottom of the image corresponds 20 nm. The structure was typical for the sol-gel derived materials. The structure was not completely condensed, but it contains a lot of small pores of about 2-5 nm in diameter, which indicates that structure is formed from smaller silica units.

Example 3

Biodegradation of Fibres

Figure 5:
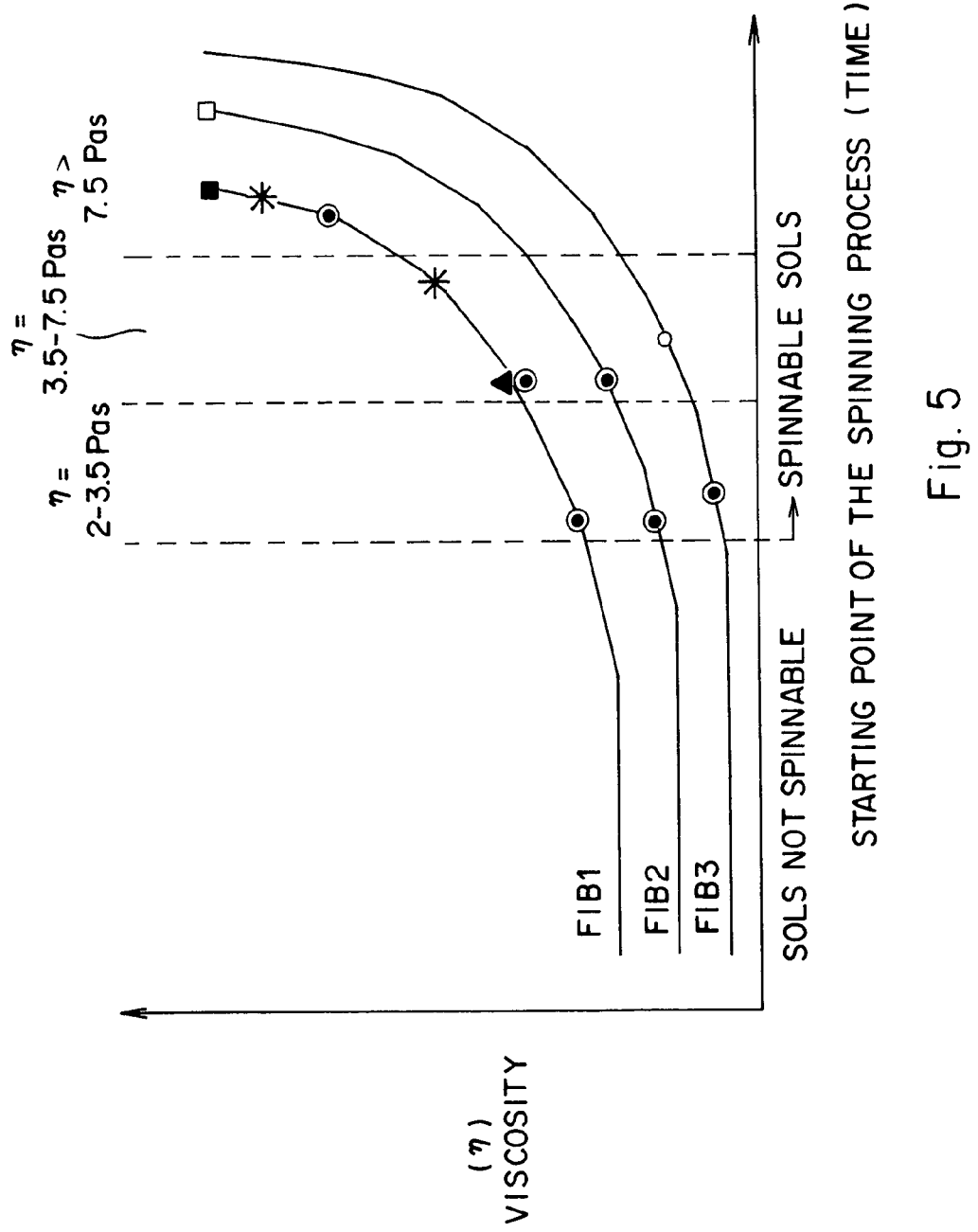
FIG. 5 shows the spinning viscosity as a function of the starting point of the spinning process for fibres FIB1, FIB2 and FIB3. Closed square (■) aged for 1 month, open square (□) aged for 2 months, closed triangle (▲) aged for 1 month and for 3 months, closed circle (●) aged for 1 month, 3 months and 5 months, open circle (○) aged for 4 months, asterisk (✳)aged for 6 months.

The spinning viscosity as a function of the starting point of the spinning process is presented in FIG. 5. The graph describes schematically the viscosity levels of the spinning sols and ageing times for the fibres FIB1, FIB2 and FIB3 before the biodegradation test in the simulated body fluid.

The spinning viscosities are roughly divided into three levels (η(1)=2000-3500 mPas, η(2)=3500-7500 mPas, and η(3)>7500 mPas.

The biodegradation of the samples was studied in vitro using a simulated body fluid (SBF). The simulated body fluid was prepared by dissolving the reagent chemicals of NaCl, NaHCO$_3$, KCl, K$_2$HPO$_4$.3H$_2$O, MgCl$_2$.6H$_2$O, CaCl$_2$.2H$_2$O and Na$_2$SO$_4$ into deionised water. The fluid was buffered at a physiological pH 7.40 at 37° C. with tris(hydroxymethyl) aminomethane and hydrochloric acid (Ohtsuki, C, et al., *J. Non-Cryst. Sol.*, 143 (1992) 84-92).

Three pieces of each specimen were used to study the reactions of the sol-gel derived silica fibres in SBF. Each sample (10 mg) was immersed in 50 ml of SBF contained in a polyethylene bottle covered with a tight lid. Three samples of SBF enclosed in bottles without a specimen were used as controls to examine the solution stability. The samples were immersed in the SBF fluid for 2 weeks, the bottles being placed in a shaking water bath (SBD 50 (stroke 36 mm, speed=160 strokes/minute)) having a constant temperature at 37° C. Sample solutions were monitored for silicon and calcium concentrations as a function of immersion time. The calcium concentrations were determined with atomic absorption spectrophotometer (AAS, Perkin-Elmer 460). The silicon concentrations were analysed by a molybdenum blue-method (Koch, O. G. & Koch-Dedic, G. A., Siliconmolybdanblau-Verfahren. In *Handbuch der Spurenanalyse*. Springer-Verlag (1974), p. 1105) based on reduction with 1-amino-2-naphtol-4-sulfonic acid using a UV-Vis spectrophotometer (Hitachi Model 100-60). All samples were tested three times each in order to avoid inaccuracy problems and possible degradation differences depending on the distribution in the cross-sectional diameter of the fibres (30-80 m, medium value 50 m). The biodegradation (in vitro in the simulated body fluid) of the green state fibres FIB1_A, FIB1_B, FIB2_A, FIB2_B, and FIB3 aged for about one and three months is summarised in Table 3.

TABLE 3

Silica solubility of the fibers soaked in the SBF

| Fiber Name | Aging time/Months | Silica solubility in SBF/wt %/h* |
|---|---|---|
| FIB1_A | 1 | 0.02 |
| FIB2_A | 1 | 0.03 |
| FIB1_B | 1 | (0.8)** |
| FIB2_B | 1 | (0.9)** |
| FIB3 | 1 | 1.7 |
| FIB1_A | 3 | 0.03 |
| FIB2_A | 3 | 0.2 |
| FIB1_B | 3 | 0.7 |
| FIB2_B | 3 | 0.8 |
| FIB3 | 3 | 1.4 |

*Calculated from the linear portion of the curves before the saturation level between 5 to 53 h of immersion.
**Estimation, the point at ~50 h is missing due to technical problems.

The same kind of analogy observed in the TG analysis and FT-IR measurements was also observed here. The fibres spun in the early stage of spinnability (FIB1_A and FIB2_A) degraded very slowly when compared to fibres spun in the later stage (FIB1_B, FIB2_B). FIB3 again had some kind of intermediate properties. According to the obtained results, some kind of plateau value or a saturation level was achieved after few days of immersion in the SBF. The solubility rates (before the plateau level) of FIB1_B, FIB2_B and FIB3 were clearly faster than for FIB1_A and FIB2_A. This indicates that the area of silica available for the degradation is greater in the structure of the fibres spun in the later stage of spinnability. As observed in Table 3, there were some differences in the degradation if the samples aged for 1 or 3 months were compared to each other. A clear difference was observed in FIB2_A. The rate of solubility was greater for the sample aged for 3 months, as was the silica saturation level (~2% for the sample aged for 1 month and ~5% for the sample aged for 3 months). For the fibres spun in the later stage (FIB1_B, FIB2_B and FIB3) there were no significant differences after 1 or 3 months of aging. The values were practically the same indicating that the structures were quite stable. However, they all were clearly more soluble in the SBF than the fibres spun in the early stage of spinnability.

In FIG. 6, the biodegradation of the green state fibres FIB1_A, FIB1_B, FIB2_A, FIB2_B, and FIB3 aged for about three months is presented.

Further, the biodegradation of fibres FIB1, FIB2 and FIB3 in vitro in the SBF is presented in FIGS. 7 to 12. In FIGS. 7 and 8, the biodegradation of the fibre FIB1 aged for about two weeks, and three, five and 6.5 months is presented. The biodegradation of the fibre FIB2 aged for about two weeks, and two, three, and five months is presented in FIGS. 9 and 10. Further, the biodegradation of the fibre FIB3 aged for about two weeks, three, four and five months is presented in FIGS. 11 and 12.

The influence of the starting point of the spinning process to the biodegradation of the fibres is clear. The main parameters, which affect the viscosity, are the concentration, length and degree of branching of silica polymers. In turn, these factors affect the formation of fibre structure, e.g., packing and orientation of silica polymers, and result in different biodegradation.

The fibres derived from the sols which have low viscosity during the spinning process degrade slower than fibres derived from sols prepared at higher spinning viscosity. Accordingly, the starting point of the spinning process is important regarding the biodegradation. The fibres spun from in the early stage of spinnability degraded very slowly as compared to fibres spun in the later stage.

It was observed that the solubility rate of FIB1 (determined from the linear portion of the corresponding solubility curves) was lower at very high spinning viscositsies, although the saturation levels did not change significantly. This is assumed to occur because the slightly thinner fibres with smoother surfaces which are produced at very high spinning viscosities.

In FIG. 13 the changes of SiO$_2$-concentration (wt-%) as a function of immersion time in the simulated body fluid for different fibres are presented. These results show that a wide range of different solubilities is covered by adjusting the properties of the silica sol.

Example 4

Preparation of Silica Fibres Containing Dexmedetomidine Hydrochloride

A sol for the fiber spinning was prepared from TEOS, deionized water, ethanol and HNO$_3$ as a catalyst in 1/2.35/1/0.000322 ratio using the sol gel method. Ethanol was mixed with TEOS and nitric acid with water. The acid/water solution was added to the TEOS/ethanol solution under vigorous stirring and then the solution was poured in an evaporating dish.

The evaporation process was performed as described in Example 1. Dexmedetomidine hydrochloride (HCl) was added after the ethanol evaporation (corresponding to 1 wt-% in dried fibre). Viscosity was 5600 mPas when the spinning process was started. The fibres were spun at four different stages of spinnability at 20° C. The fibres were packed and stored air tightly in aluminium folio bags at room temperature until the dissolution tests were carried out.

In Vitro Dissolution Test

The dissolution profiles of dexmedetomidine HCl from the silica fibres were studied using dissolution apparatus II (paddle method, Sotax AT6, Basel, Switzerland). Each sample (50 mg) was immersed in 250 ml of 0.9 wt-% NaCl solution. The rotation speed was 50 rpm and the temperature 37° C. Dissolved dexmedetomidine HCl in the dissolution samples was measured on an UV-visible spectrophotometer (Hewlett Packard 845/A, USA) at the maximum absorbance of dexmedetomidine HCl, 220 nm.

Results

The release of dexmedetomidine HCl showed a burst (33%) at the spinning viscosity lower than 10 000 mPas (FIG. 14). When the spinning viscosity was increased to more than 11500 mPas, the burst effect was decreased to 3-10%. At spinning viscosity above 11500 mPas the release rate of dexmedtomidine HCl was decreased compared to fibres spun lower than 11500 mPas.

Those skilled in the art will recognize that while specific embodiments have been illustrated and described, various modifications and changes may be made without departing from the spirit and scope of the invention.

The references discussed herein are specifically incorporated by reference in their entity.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A biodegradable silica fibre spun from silica sol, a biodegradation rate of said fibre being adjusted by controlling the starting point of the spinning process by a viscosity of the silica sol wherefrom the fibre is spun, said fibre having a solubility rate in simulated body fluid of 0.2 to 20 wt-%/h.

2. A delivery device comprising the biodegradable fibre according to claim 1, wherein the fibre contains a biologically active agent.

3. The delivery device according to claim 2, wherein said biologically active agent is a medicine, a protein, a hormone, a living or dead cell, a bacteria, a virus or a part thereof.

4. The delivery device according to claim 3, wherein said biologically active agent is a medicine.

5. A pharmaceutical preparation comprising a delivery device according to claim 2.

6. A method for administering a biologically active agent to a human or animal, wherein said method comprises implanting, injecting or mucosally attaching a delivery device, wherein said delivery device comprises a biodegradable fibre according to claim 1 and wherein the fibre comprises a biologically active agent.

7. The method according to claim 6, wherein the biologically active agent is administered into a mammal.

8. A biodegradable silica fibre according to claim 1, the solubility rate of the fibre in simulated body fluid being 0.2 to 8.5 wt-%/h.

9. A biodegradable silica fibre spun from a silica sol, a biodegradation rate of the fibre being adjusted by controlling the viscosity of the spinning sol wherefrom the fibre is spun, said fibre having a solubility rate in simulated body fluid of 0.2 to 20 wt-%/h.

10. A biodegradable silica fibre according to claim 9, the solubility rate of the fibre in simulated body fluid being 0.2 to 8.5 wt-%/h.

* * * * *